United States Patent [19]

Wilkins

[11] Patent Number: 5,528,431
[45] Date of Patent: Jun. 18, 1996

[54] APPARATUS FOR OBTAINING A DESIRED TINT

[75] Inventor: Arnold J. Wilkins, Cambridge, England

[73] Assignee: Cerium Group Limited of Hill House, London, United Kingdom

[21] Appl. No.: 975,570
[22] PCT Filed: Jul. 9, 1991
[86] PCT No.: PCT/GB91/01126
  § 371 Date: Jul. 6, 1993
  § 102(e) Date: Jul. 6, 1993
[87] PCT Pub. No.: WO92/01416
  PCT Pub. Date: Feb. 6, 1992

[30] Foreign Application Priority Data

Jul. 25, 1990 [GB] United Kingdom .................. 9016307
Jun. 3, 1991 [GB] United Kingdom .................. 9111889

[51] Int. Cl.⁶ .......................... G02B 27/00; G02B 3/00; G02B 5/08; G02B 5/22
[52] U.S. Cl. .................... 359/885; 359/601; 359/722; 359/884; 359/889; 356/405
[58] Field of Search .................. 359/885, 889, 359/891, 892, 568, 884, 722, 601

[56] References Cited

U.S. PATENT DOCUMENTS

| | | | |
|---|---|---|---|
| 2,649,017 | 8/1950 | McCarty | 356/404 |
| 2,684,010 | 7/1954 | Bulkley | 356/423 |
| 3,166,672 | 1/1965 | Gardner | 359/889 |
| 3,442,572 | 5/1969 | Illsley et al. | 359/578 |
| 3,653,771 | 4/1972 | Piringer | 356/194 |
| 4,019,819 | 4/1977 | Lodzinski | 356/73 |
| 4,549,787 | 10/1985 | Tanner | 359/889 |
| 4,797,000 | 1/1989 | Curtis | 356/436 |
| 4,838,697 | 6/1989 | Kurandt | 356/406 |
| 4,894,760 | 1/1990 | Callahan | 359/889 |
| 4,909,633 | 3/1990 | Okui et al. | 356/405 |
| 5,231,559 | 7/1993 | Kalt et al. | 361/301.5 |
| 5,272,518 | 12/1993 | Vincent | 356/405 |
| 5,422,755 | 6/1995 | Morgan | 359/361 |
| 5,438,024 | 8/1995 | Bolton et al. | 501/55 |

Primary Examiner—Paul M. Dzierzynski
Assistant Examiner—M. Sikder
Attorney, Agent, or Firm—Dickinson, Wright, Moon, Van Dusen & Freeman

[57] ABSTRACT

Apparatus for obtaining a desired tint, which apparatus uses a light source to provide a gamut of colours. The apparatus comprises wheel and paddle (34,60) which enable a tint to be obtained from such light in such a manner that the hue and saturation of the tint can be varied substantially independently of one another, whilst maintaining a given brightness. The invention extends to a method using such apparatus, and to equipment comprising a set of coloured filters, and also to a method in which a tint created by a combination of filters selected from a set of filters is varied, by removal, addition, or replacement of one or more filters of the combination, to match the selected tint, and finally to the making of lenses using such methods, and the lenses themselves.

8 Claims, 17 Drawing Sheets

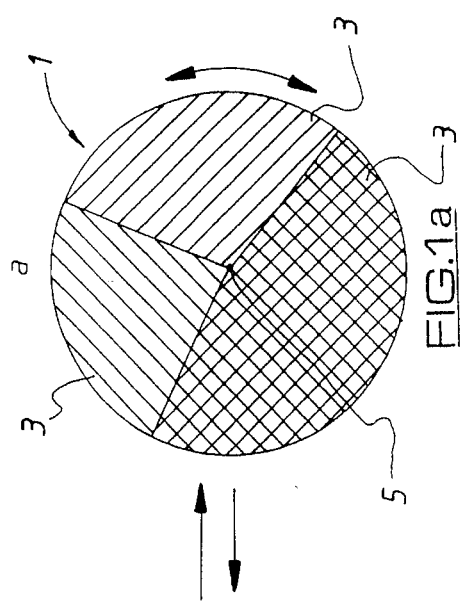
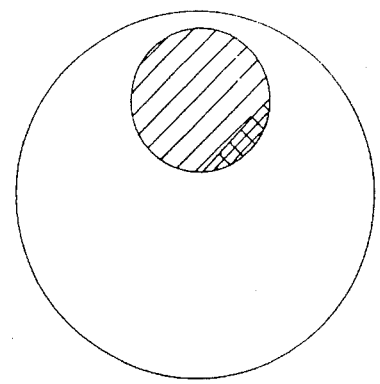
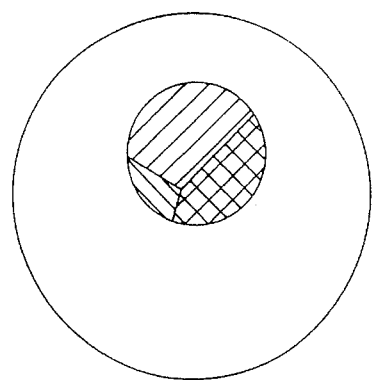
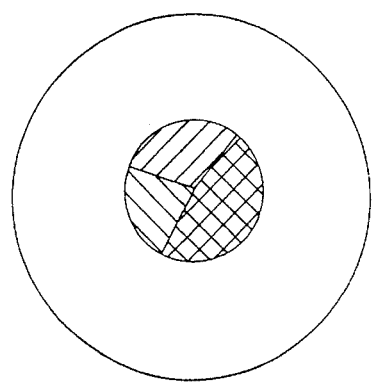

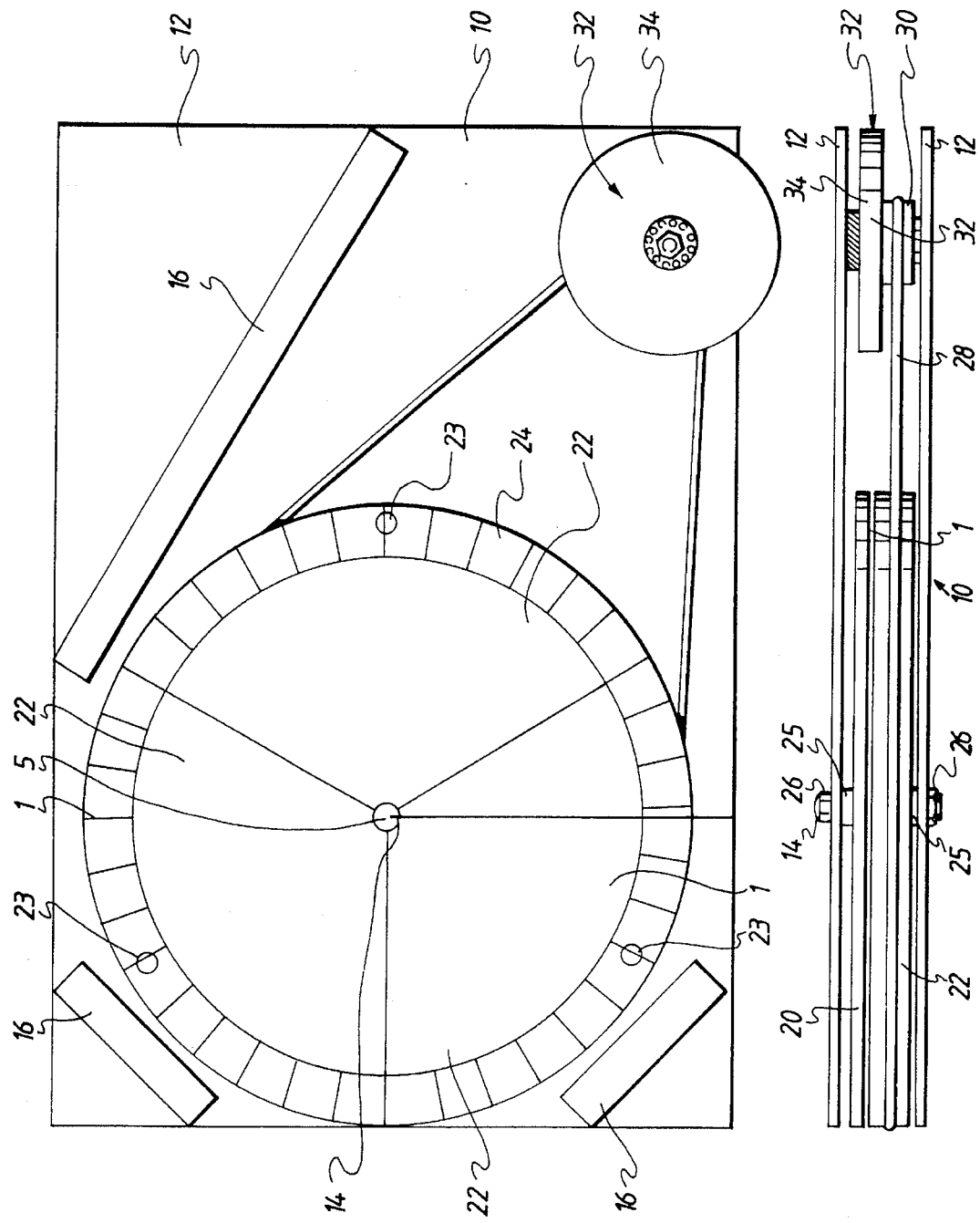

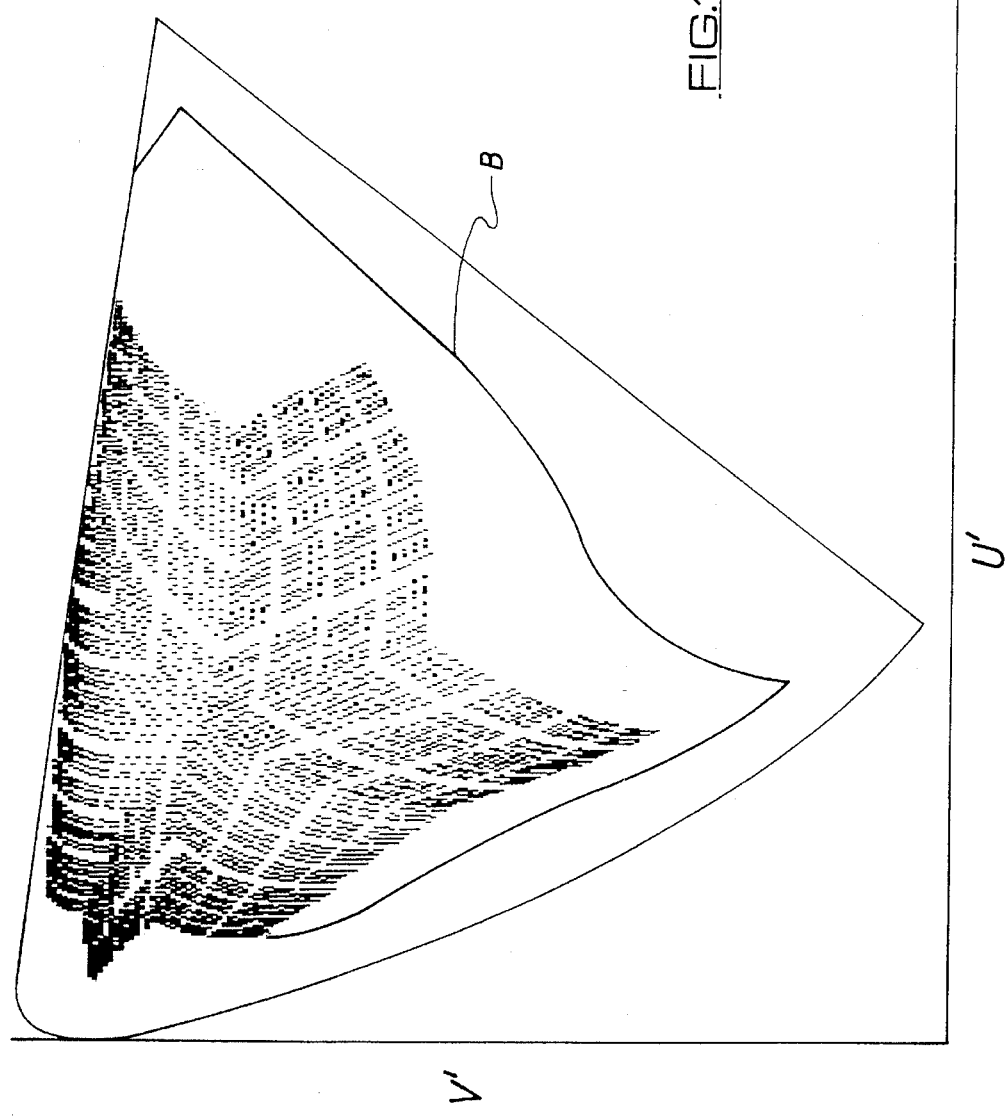

APPARATUS FOR OBTAINING A DESIRED TINT

BACKGROUND OF THE INVENTION

The present invention relates to apparatus for and a method of obtaining a desired tint.

Such a tint may be used to alleviate visual discomfort in a number of circumstances. For example, flicker can cause seizures in up to 4% of patients with epilepsy. Such flicker may be caused by a television, because the lines that make up the pictures are scanned 25 times per second, and in addition the whole screen may flash 50 times per second owing to the frequency associated with the power source. Both sources of flicker can cause seizures in epileptics. Flicker is not noticeable at frequencies of about 100 flashes per second and beyond, but it nonetheless affects the firing of cells in the retina and parts of the brain. Such rapid flicker is present in a picture given by a visual display terminal, and also in the illumination produced by fluorescent lighting. Both of these sources affect eye movements. Fluorescent lighting in particular can cause eye-strain and headaches. With most fluorescent lamps the rapid flicker is greatest for the blue and green components of white light. So it has been found that rose-brown tinted spectacles reduce the flicker. Similarly such spectacles reduce the likelihood of headaches in people who use visual display terminals under fluorescent lighting, and also in children who suffer from periodic syndrome, which is a form of migraine.

Certain patterns can be unpleasant to look at. Such patterns may cause seizures in some patients with epilepsy who are sensitive to flicker. Such unpleasant patterns may cause anomalous perceptual effects, such as illusions of colour, shape and motion. However, some people are more susceptible to these effects than others. The discomfort and illusions from patterns are common in migraine, and may be related to immune system dysfunction.

Particularly bad patterns in this respect are striped, or have elements that form stripes. Successive lines of printed text resemble stripes (although such "stripes" are not as bad as continuous stripes). Some people are so sensitive to patterns that they see anomalous perceptual effects in text. Covering the lines of text above and below those being read reduces these effects.

Children with reading difficulty often have deficits on certain visual tasks and not others. The deficits suggest a dysfunction of the so-called "transient" system. Children with reading difficulties often report anomalous perceptual effects in text, but the relationship with the selective "transient" deficits is not yet know.

It has been found that some individuals no longer perceive the distortions described hereinabove when text is illuminated by coloured light, provided the colour is within a specific range that depends on the individual. The range of colours can be very small, and stable. It is unusual for the range to include shades of red. When colours with different saturation are compared, those with similar hue are preferred. There is usually also a range of colours that makes the distortions worse. Within this range discomfort or pain may occur. The discomfort can be assessed by observation of behaviour as well as subjective report. The uncomfortable colours are usually complementary to those that reduce perceptual distortion.

There has previously been proposed a technique for selecting appropriately tinted spectacles. Such children who seem to benefit from coloured overlays, are invited to undergo a one to two hour procedure to select an appropriate tint. Such a child goes through a large set of trial tints, picking out those that appear to make it easier for the child to view a page of text that has been written in a language which is foreign to the child. (A foreign text is used to emphasise the visual rather than the semantic aspects of reading). The examiner asks the child to describe the visual distortions he sees using his own words, and then employs this description when comparing the lenses. By a lengthy process of elimination the best tint is eventually selected and other tints added to fine-tune the colour. The selection eventually arrived at can involve a combination of three or more tinted trial lenses and the combination is often quite dark. This might be partly because one colour is being added to another to get the right tint. From this examination a code for the selected lenses is thus provided.

In order for patients to select a tinted lens it has been necessary in the past for the patient to view through varying numbers of coloured filters. A problem 10 with this method is the time-consuming number of operations involved in obtaining the desired tint.

SUMMARY OF THE INVENTION

The present invention seeks to provide a remedy.

Accordingly, the present invention provides apparatus for obtaining a desired tint, which apparatus uses a light source to provide a gamut of colours, the apparatus comprising control means which enable a tint to be obtained from such light in such a manner that the hue and saturation of the tint can be varied substantially independently of one another, whilst maintaining a given brightness.

In a preferred embodiment of this invention, the control means comprise a plurality of regions of respective different colours, each region being contiguous with two others along respective lines, and the plurality of lines of contiguity meeting at a common point.

The said regions may be reflective surfaces or transmission filters, and may be parts of a circular disc, for example radial sectors of a disc.

The control means may further comprise light directing means which serve to direct light towards an illuminated area that is moveable relative to the said regions so as to be incident upon parts of any two or more of the said regions.

Variation in hue may be effected by a relative circular movement of the said area about the said common point, and variation in saturation may be effected by relative radial movement of the said area towards or away from the said common point. To effect the circular movement the said regions may be mounted so as to be rotatable about the said common point, and to effect the radial movement, those regions may be mounted so as to be moveable linearly.

Preferably the said regions are contained in a replacement cartridge at least part of which is transparent to expose those regions.

Advantageously, light which forms the said tint is mixed by a plurality of opal filters and an integrating bar of the apparatus.

Preferably, though, the light which forms the said tint is mixed by multiple reflection. This may be effected by means of internal surfaces of an enclosure of the apparatus. The internal surfaces may be white.

Whilst it would be conceivable to use natural light as the light source, it is preferable for the apparatus to include its own light source, preferably a white light source.

The apparatus may have measuring means to provide measures of the hue and saturation.

Preferably the apparatus further comprises an enclosure having internal surfaces which are white or which are of a uniform colour, the enclosure having a first aperture by which light of more than one colour from such a light source may be directed into the enclosure, and a second aperture by which the interior of the enclosure may be viewed, the first and second apertures and the internal surfaces of the enclosure being so arranged that the tint of light observed through the second aperture is a mixture of the colours of light which enter through the first aperture, the mix being effected by multiple reflection.

Means may be provided for the insertion of a sheet bearing printed matter into the enclosure so as to be observable from the said second aperture, illuminated by the mixed light.

Advantageously, the apparatus has comparison means comprising a viewing port to view the enclosure interior, and a reference light source in the form of a port positioned alongside the viewing port.

Preferably, the enclosure, apart from the said apertures, is light-tight.

Advantageously, the apparatus further comprises a set of coloured filters in which at least a first one of the set has a colouring strength which is greater than that of a second one of the set, and a third one of the set has a colouring strength which is greater than the said first one of the set, so that a linear or logarithmic increase in colouring strength is obtained from successive selections from the set as follows: firstly the said second filter; secondly the first and second filters together; thirdly the said third filter on its own; then the third and first filters; then the third and second filters; then the first, second and third filters. The advantage of this series is that with a series of five such addition filters a total of 31 combinations of colour strength are possible.

The present invention extends to a method of obtaining a desired tint, from a gamut of colours, in which a light source is used to provide such a gamut, the tint being obtained by varying the hue and saturation of a combination of colours from such light independently of one another, whilst maintaining a given brightness.

The variation in hue and saturation may be effected by means of a plurality of regions of respective different colours, each region being contiguous with two others along straight lines, and the plurality of lines of contiguity meeting at a common point. The light may be reflected from or transmitted through the said regions.

Light from such a source may be directed onto an area of the said regions, and may be moveable relative thereto, so as to be incident upon parts of any two or more of the said regions, thereby to enable the said variation to be made.

The said area may be moved circularly, relative to the said regions, about the said common point, to vary the hue of the combination, and radially to vary the saturation.

Such movement may be brought about by moving the said regions. The light from these regions is preferably mixed by multiple reflection.

Measuring means may be used to provide measures of the hue and saturation of the selected tint.

In a further step, a tint may be created by varying a combination of filters selected from a set of filters, by removal, addition, or replacement of one or more filters of the combination, to match the selected tint. An initial selection of filters may be made on the basis of the measures of hue and saturation.

An optical lens may be prepared having a selected tint, in accordance with the measures of hue and saturation. This may be done by tinting the lens in accordance with the aforementioned selection of filters.

The number of the said plurality of regions is preferably three.

Thus an example of apparatus made in accordance with the present invention may be so constructed that it enables an observer to change the colour of light falling on a page of text by turning a wheel. A lever may be provided by means of which the observer can vary the saturation of the hue from near white to strongly coloured. None of these changes affect the brightness of light on the page: this can be changed using a separate control if desired. Such apparatus may be referred to as an intuitive colorimeter. It has three important advantages for studying the effects of colour on reading.

1. The observer can change just one variable at a time: because the hue, saturation or brightness can be varied substantially independently of the other, it is easier to separate their effects, and the child knows or can readily learn how to obtain a particular shade.
2. Colour can be varied continuously so that an infinite number of colours are obtainable from the range or gamut that is available from the apparatus. In this respect, the observer is not restricted to a number of discrete colours.
3. No surfaces within the apparatus reflect light of one colour more than that of any other colour. Therefore if brightness is held constant, only two variables (the hue and saturation of the illuminating light) are important. This simplifies matters considerably.

The tint obtained by such apparatus closely matches that obtained by the Irlen system for about eight out of nine children examined. A combination of tinted trial lenses closely matching the obtained tint can reduce visual discomfort experienced by the observer in everyday surroundings. The range of cosmetic and ophthalmic tints currently available to opticians is insufficiently large to obtain the desired tint.

It is sometimes necessary to reduce the saturation of the colour of the tint actually prescribed relative to that of the colour obtained by means of the apparatus to prevent white surfaces appearing coloured. The tint obtained is usually found to be satisfactory under both fluorescent lighting and natural daylight. When spectacles with the appropriate tint are worn, eye-strain and headaches are reduced. The attitude to reading of the child wearing the spectacles may change. The physiological basis for the therapeutic effects is unknown and may well involve various factors. It may involve cortical inhibitory mechanisms.

BRIEF DESCRIPTION OF THE DRAWING

An example of apparatus made in accordance with the present invention will now be described with reference to the accompanying drawings, in which:

FIG. 1a shows a main face of part of such apparatus, isolated from the rest of the apparatus for explanatory purposes;

FIG. 1b to 1d show the part illustrated in FIG. 1a, with different areas thereof illuminated;

FIG. 2 shows a top view of a cartridge of the apparatus, incorporating a modified form of the part illustrated in FIG. 1a;

FIG. 2a shows a side view of the cartridge illustrated in FIG. 2;

FIG. 11b shows a baricentric plot of the relative areas of PXY, PYZ and PXZ produced by the part shown in FIG. 11a;

FIG. 12a shows a main face of a modified form of the part shown in FIG. 11a;

FIG. 12b shows a baricentric plot of the colours produced by the part shown in FIG. 12a;

FIG. 17 is a further UCS chromaticity diagram showing the tints that can be obtained from those filters.

DESCRIPTION OF THE PREFERRED EMBODIMENTS

Figure 3:
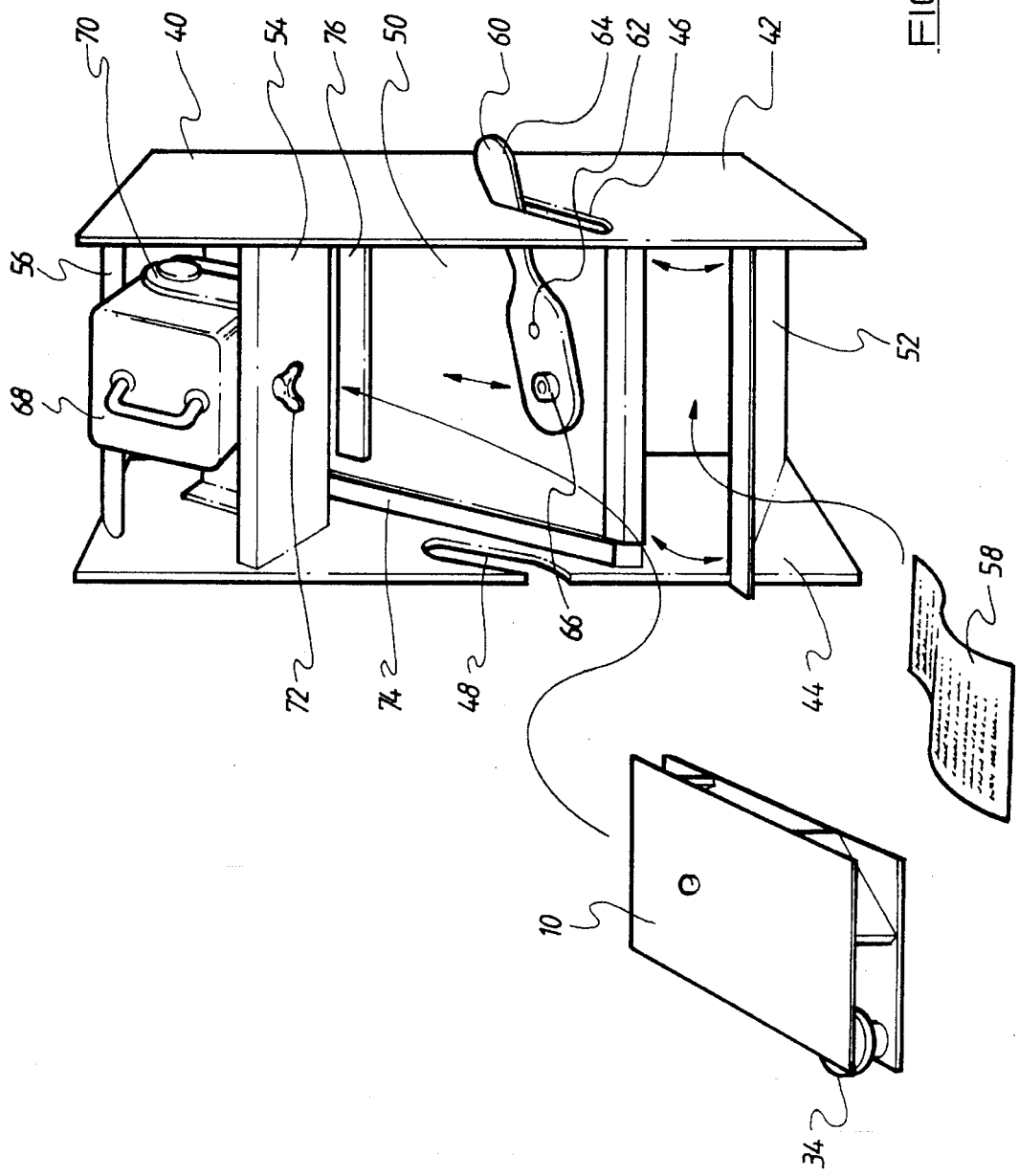
FIG. 3 shows a perspective view of the apparatus from the rear and to one side, with the cartridge thereof removed for the sake of clarity.

A transparent disc 1 shown in FIG. 1a has three filters 3 attached to it so that one sector of the disc appears to be coloured red, another green and a third blue. Multiple layers of filter material are used together with filters affecting the transmittance of the sector but not the colour, so that the photopic energy emitted by each sector is the same or subtantially the same. The disc 1 is free to rotate about a central axis 5, and the axis 5 is free to translate or move laterally. Collimated white light is directed along a beam onto the disc to illuminate and pass through a circular area having a diameter less than half that of the disc 1. The light which passes through the disc is subsequently mixed by multiple reflection, as will be described hereinafter in greater detail. The proportion of red, green and blue light transmitted depends on the position of the beam with respect to the disc 1. When the beam and the disc 1 are concentric (FIG. 1b) the area of the sectors can be such that the three primary colours are mixed in a proportion appropriate to produce a suitable reference white (for example so as to have the chromaticity of standard daylight). Provided the beam is diffuse, rotation of the disc with the illustrated area control is without effect. The disc 1 is free to move laterally, so that the beam of light can pass through the disc 1 eccentrically. When the beam and disc 1 are eccentric (as for example in FIGS. 1c and 1d), the chromaticity of the mixture departs from white. To a first approximation, the hue of the mixed light can then be varied by rotating the disc 1, and the saturation can be increased by translating the disc 1 so that the eccentricity is increased. In this way, hue and saturation can be varied substantially independently of one another. However, when the separation of the centres of the beam and the disc 1 is large (as in FIG. 1d) hue and saturation may vary together. The luminance of the mixture can be varied using any of the standard methods, for example by means of a rheostat in the circuitry which powers the light source, or by interposing a fine metal mesh in the light path so as to keep the colour temperature of the light constant.

FIGS. 2 and 2a show a cartridge 10 containing a disc 1 with equal sectors. The cartridge 10 comprises two rectangular perspex or other transparent material plates 12. The disc 1 is held between the two plates 12 on a spindle 14, which extends through the axis 5 of the disc 1. The plates 12 are held parallel and spaced apart by three spacers 16 which are positioned so as not to interfere with the rotation of the disc 1.

The disc 1 comprises a transparent top part 18 and a transparent bottom drive part 20. The three coloured sectors 3 are held between the two parts 18 and 20 of the disc 1, the upper and lower parts being secured together by three screws 23. A scale 24 is mounted round the edge of the disc 1, a line 24a is marked on the intended top plate 12 to enable accurate readings of the position of the disc 1 to be made. The disc 1 is held clear of the surfaces of the two plates 12 by washers 25 on the spindle 14 between the disc 1 and the plates 12. The spindle 14 is secured on the outside of both plates 12 by nuts 26.

The disc 1 can be rotated by a drive band 28 which extends around the periphery of the lower part 22 of the disc 1 and also around a pulley 30 of adjustment control 32, rotatably mounted between the plates 12. The adjustment control 32 is also provided with a wheel 34 mounted on the pulley 30. The control 32 is mounted between the plates 12 at one corner of the rectangular cartridge 10 so that the wheel 34 projects beyond the edges of the plates 12. Thus a user can rotate the disc 1 by rotating the wheel 34, the band drive effecting a gearing between the control 32 and the disc 1 so that a relatively fine adjustment can be achieved.

FIG. 3 shows a colorimeter 40 for receiving the cartridge 10. The colorimeter 40 has two parallel upright side walls 42 and 44. One side wall 42 has an elongate hole 46 cut in it, slanting in an upward direction. The other wall 44 has a similar slot 48 cut in it which is open at the intended back of the colorimeter 40. Between the parallel side walls 42 and 44 extend a slanted rear wall 50, an access hatch wall 52 at the bottom of the colorimeter, a lamp support 54 and a top tying bar 56. The access hatch wall 52 is mounted so as to be pivotable about a front edge thereof, between a closed position in which its upper rear edge abuts the bottom edge of the slanted rear wall 50 and an open position in which sheets of text 58 can be inserted through the gap between the walls 50 and 52. The slanted back wall 50 is equipped with a paddle 60 mounted on a pivot 62, at the middle part of the paddle 60, on the back of the rear wall 50. A handle end 64 of the paddle 60 extends through the slot 46 in the side wall 42. A roller 66 is mounted at the other end of the paddle 60.

A theatre light 68 is held on the lamp support 54 towards the top of the colorimeter 40 by a bracket 70 which passes through the support 54 and is held in place by a wing nut 72. The lamp 68 is angled so as to be perpendicular to the slanted rear wall 50, and there is a space between the slanted rear wall 50 and the lamp 68 and its support 54 for the cartridge 10 to fit through. A cartridge guide 74 which comprises an elongate piece, rectangular in cross section, is mounted on the slanted rear wall against the side wall 44 (not shown in FIG. 3, but shown in FIG. 4). A cartridge spacer 76, which is an elongate piece with rectangular cross-section, is mounted across the slanted rear wall 50 approximately level with the lamp support 54.

When the cartridge 10 is inserted in the colorimeter 40, it rests on the slanted rear wall 50, on top of the spacer 76 and the paddle 60, and abuts the guides 74 and 75, and the roller 66 on the paddle 60. The wheel 32 on the cartridge 10 extends through the slot 48. The cartridge 10 can be moved upwards and downwards in front of the light 68, by using the paddle 60. As the handle 64 of the paddle is pushed down the other end of the paddle 60 rotates upwardly about the pivot 62, pushing the cartridge 10 upwardly via the roller 66. Conversely, upward movement of the handle 64 lowers the cartridge. By such linear movement of the cartridge 10, it is possible to alter the saturation of the light produced by the colorimeter. The wheel 34 allows alteration of the hue of the light produced by the colorimeter 40 by rotation of the disc 1.

Figure 4:
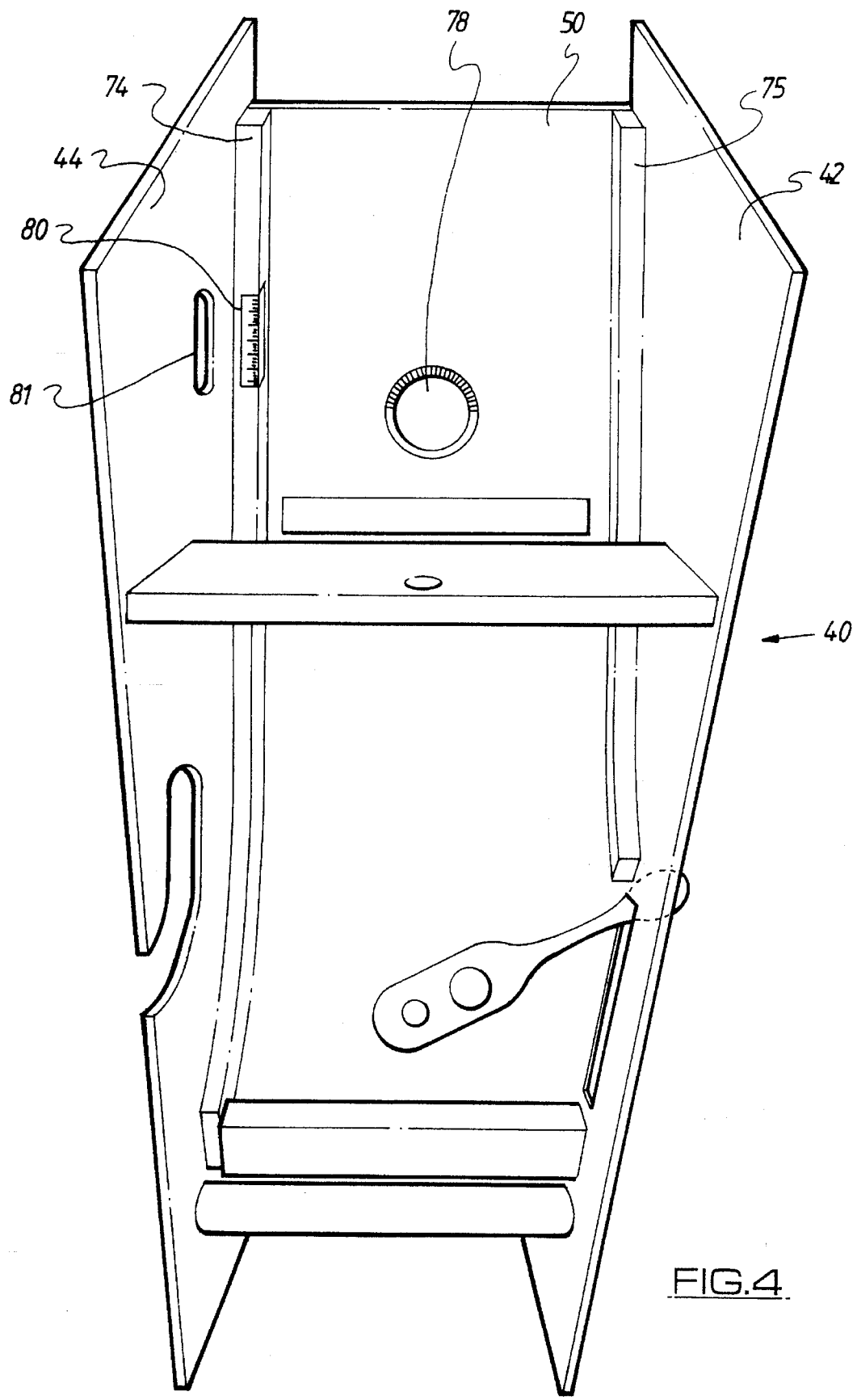
FIG. 4 shows a perspective view of the apparatus illustrated in FIG. 3 from the rear, with both the cartridge and a light source of the apparatus removed to reveal further details.

FIG. 4 more clearly shows further aspects of the construction of the rear of the colorimeter 40, the light 68 having been removed. The slanting rear wall 50 has a circular hole 78 through it, which is midway between the side walls 42 and 44 and level with the position of the lamp. There is a linear scale 80 mounted in the guide 74 just above the hole 78, in order to measure the vertical position of the cartridge 10 when the colorimeter is in use. The position of the cartridge 10 can be read off the scale 80 using the hole 81, this also enables measuring of the position of the disc 1 using scale 24 and line 24a when the cartridge 10 is in position. Therefore the saturation and the hue obtained with the colorimeter can be measured.

Figure 5:
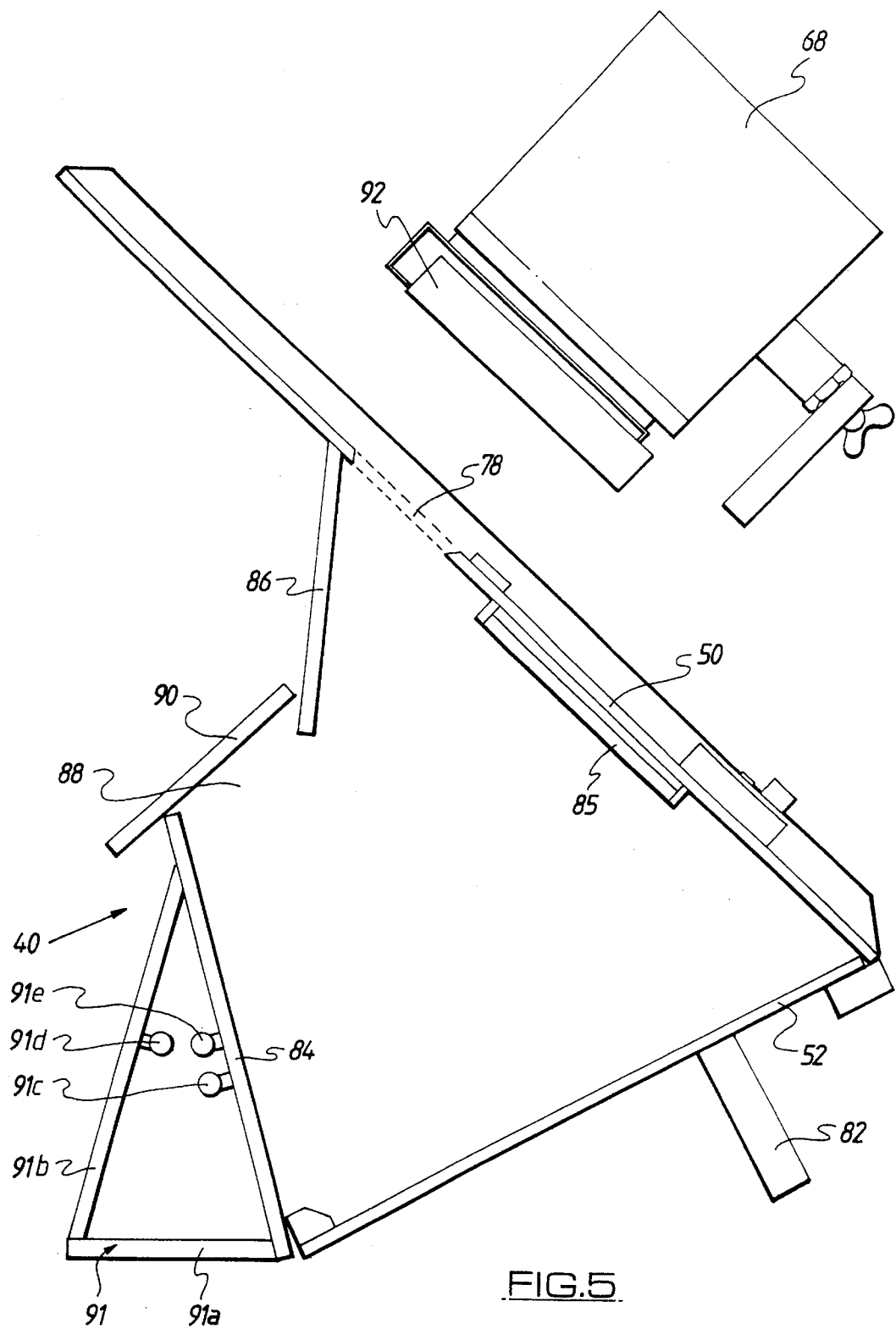
FIG. 5 shows a cross-sectional view of the apparatus illustrated in FIG. 3, in a vertical plane extending from the front to the rear of the apparatus.

FIG. 5 shows the structure of the front of the colorimeter 40. The hatch wall 52 is held in place by a latch 82. The bottom of hatch wall 52 abuts a front wall 84 of the colorimeter which is slanted forwards in the upward direction, and has approximately half the length of the rear wall 50. A flourescent light tube 85 is mounted on the rear wall 50 to enable illumination, if required, of the text 58 inside of the colorimeter 40 by such light for comparison purposes when using prepared trial filters.

A deflection wall 86 extends downwardly from a position immediately above the hole 78 in the rear wall 50, to a position a little above and rearwards of the top edge of the front wall 84. The space between the front wall 84 and the deflection wall 86 is bridged by a viewing window 88. The viewing window 88 has a shutter 90 which is hingably mounted on the deflection wall 86.

In front of the front wall 84 there is situated a reference light box 91. The light box 91 comprises two walls 91a and 91b which with the front wall 84 form a triangular enclosure. The inside surfaces of the walls of the reference light box 91 are painted white. The light box 91 contains three light sources, 91c a white tungsten light, 91d a daylight light and 91e a fluorescent light tube.

The lamp 68 is equipped with a liquid heat sink 92 on its front to absorb the heat produced by the lamp 68 when in use and to stop such heat affecting the cartridge 10. The walls 42, 44, 50, 52, 84 and 86 define a box the interior of which is painted white to ensure multiple reflection, allowing mixing of the light which enters the interior through the hole 78.

Figure 6:
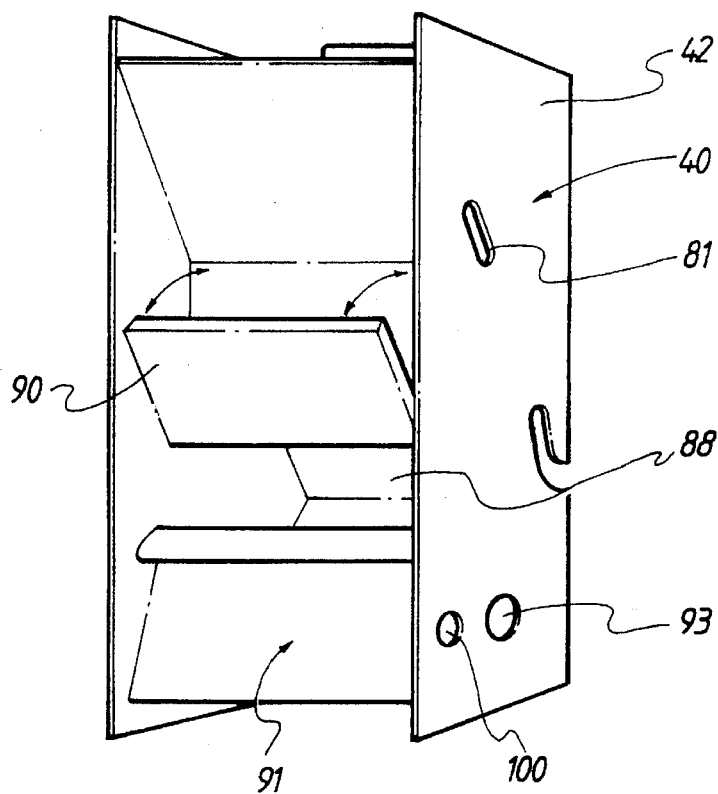
FIG. 6 shows a front perspective view of the apparatus illustrated in FIG. 3.

FIG. 6 shows the movement of the shutter 90 from its open position in which it abuts the deflection wall 86, allowing viewing through the window 88, to its closed position in which it abuts the front wall 84, thus covering the window 88.

The side wall 42 has a calibration port 93 cut in it to allow independent viewing of the tint obtained in the interior of the box of the colorimeter and similarly a reference port 100 to allow viewing of the reference light box 91.

Figure 7:
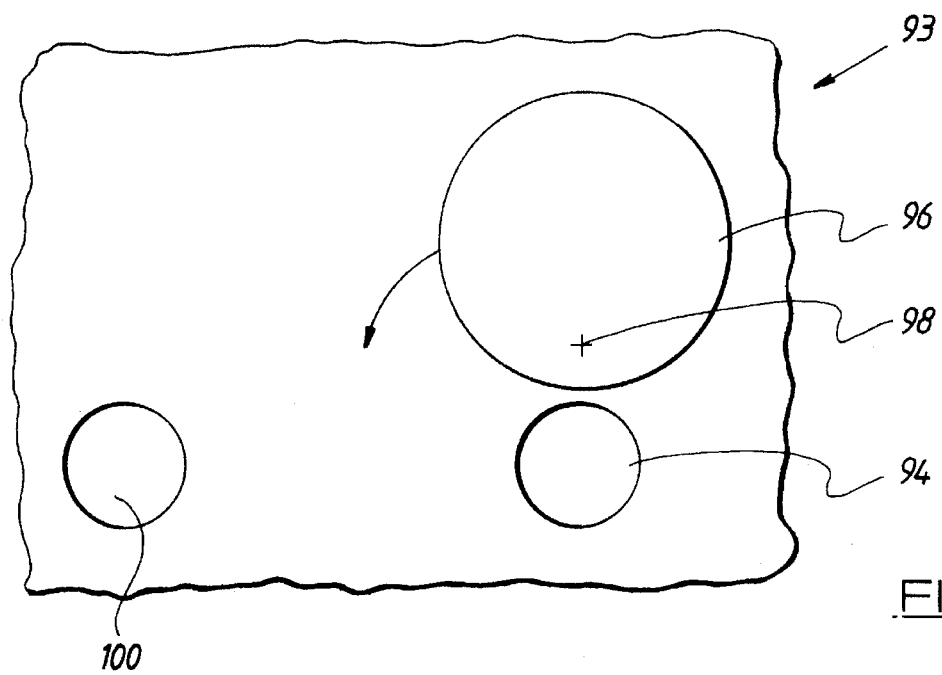
FIG. 7 shows, on a larger scale, a side view of a calibration port for the apparatus illustrated in FIG. 3.

FIG. 7 shows the calibration port 93 in greater detail. The port 93 is circular. Alongside it there is the reference port 100, level with the port 93 and of the same size. The port 93 is provided with a cover 96 which is rotatably mounted on a screw 98 above the port 93 to allow the latter to be covered when not in use. The cover 96 may be mechanically attached to shutter 90 so that only one of them can be open at any one time. The surrounds of both the port 94 and the reference port 100 are painted black.

The port 93 allows a colour analyser to analyse the colour preferred by the patient using the light from the reference port 100 as a reference or alternatively trial lenses may be compared under daylight, flourescent light or tungsten light with the colour produced by the colorimeter.

Figure 8:
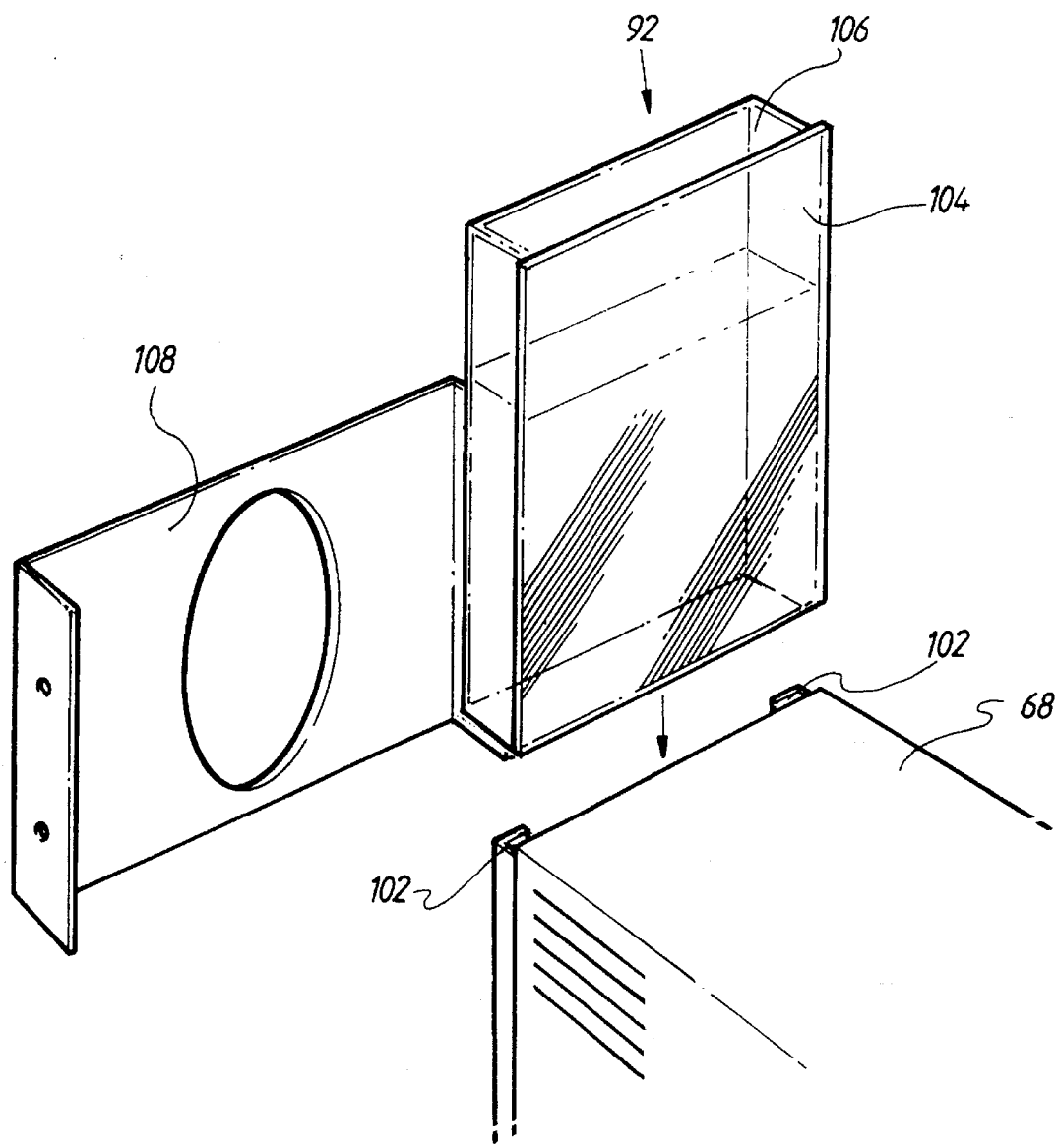
FIG. 8 shows a perspective view of a heat sink arrangement for the apparatus illustrated in FIG. 3.

FIG. 8 shows the lamp heat sink arrangement in greater detail. The lamp 68 has two elongate mounting parts 102 on the sides of its front which have a U-shaped cross-section. The parts 102 receive a back plate 104 of the liquid heat sink 92, which is thereby slid into position in front of the lamp 68. The plate 104 carries a rectangular box 106 which is mounted with its sides slightly inward the edges of the plate 104 so as not to interfere with the mounting parts 102. The box 106 contains a heat absorbing liquid such as water. A shroud 108 is mounted in front of the heat sink 92 to give the lamp 68 a clearly defined beam of light of circular cross-section.

Figure 9:
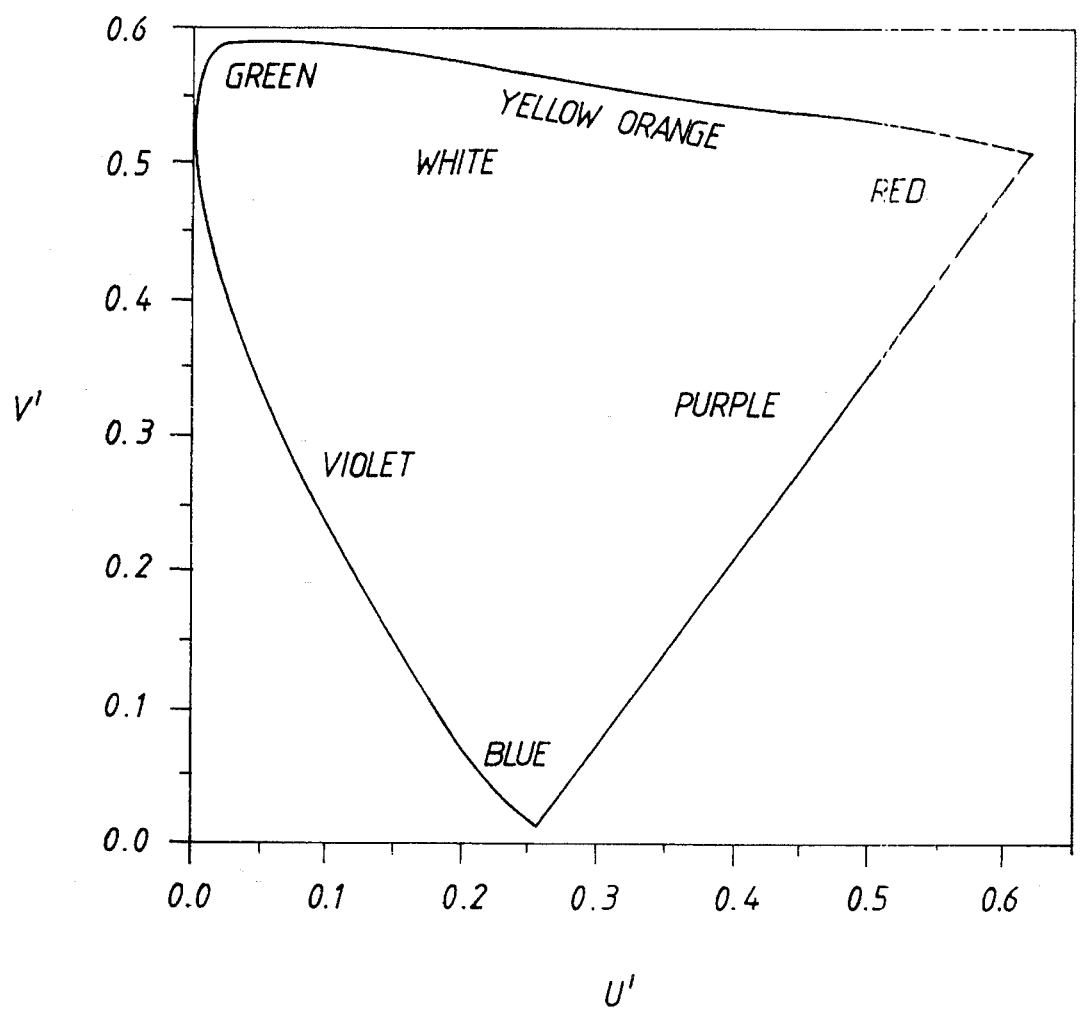
FIG. 9 shows a CIE 1976 uniform chromaticity space (UCS) diagram.

FIG. 9 shows one way of representing colour. It is a CIE 1976 uniform chromaticity space (UCS) diagram. Highly saturated colours are located around the edge of the triangular space and less saturated pastel shades towards the centre. The distance between any two points roughly corresponds to the dissimilarity of the colours. All the colours of the rainbow are represented on the so-called "spectral locus" (the curved perimeter) and the colours that are not in the rainbow such as purple are shown by the straight line joining the ends of the spectrum.

The filters in the colorimeter have broad spectral transmissions, that is, they have few local maxima and minima in their spectral transmission functions. Their transmission bands are designed so that:

(i) when the light transmitted by the three filters is mixed in equal proportions, the spectral power distribution of the light within the box is as flat as possible; and (ii) The CIE 1976 uniform chromaticity space (UCS) coordinates of the light transmitted by each filter lie close to the apices of an equilateral triangle in the UCS chromaticity diagram. The triangle has the largest area possible, given the constraint that its centre has the coordinates of daylight (D65). (The largest area is achieved when one side of the triangle is close to the spectrum locus near 575 nm.).

The filters can be manufactured by the superimposition of readily available theatrical filters.

Figure 10A:
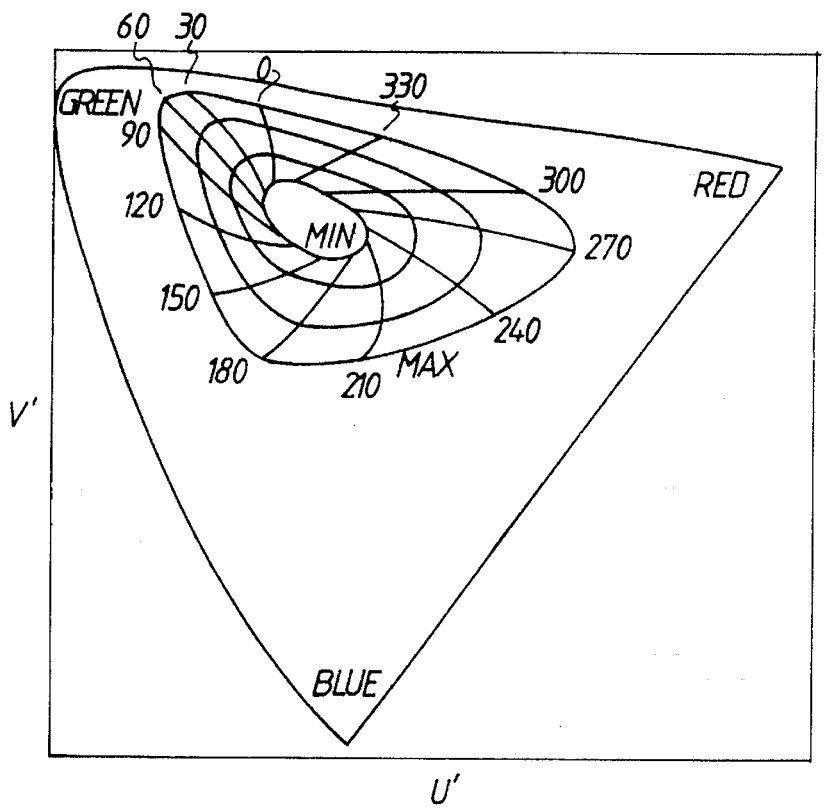
FIG. 10a shows a UCS chromaticity diagram of the colours realised by the apparatus illustrated in FIG. 3.
Figure 10B:
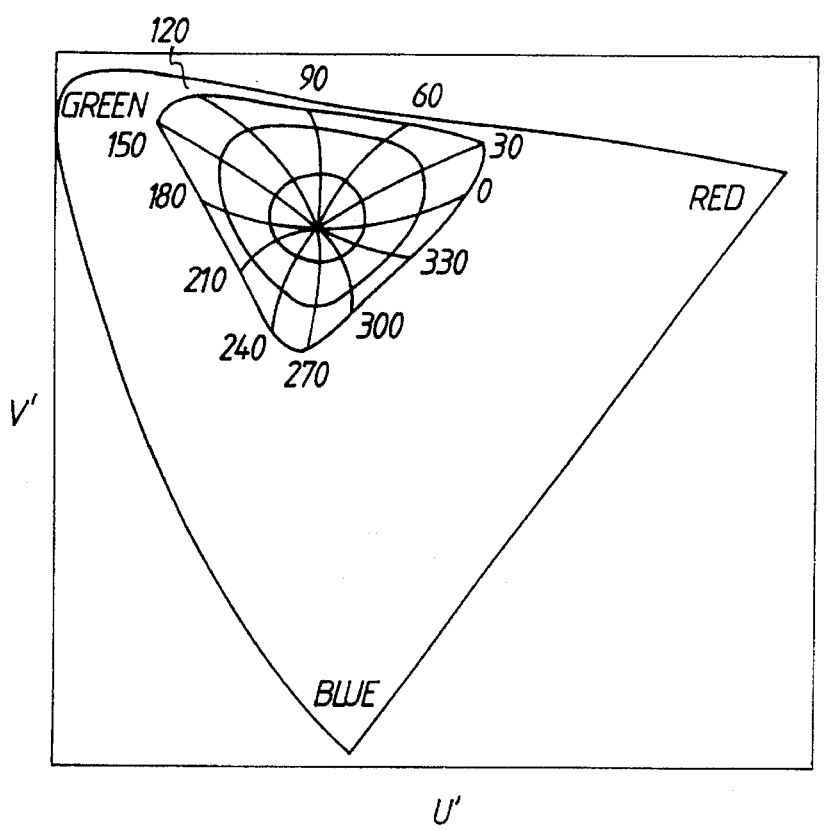
FIG. 10b shows a UCS chromaticity diagram similar to that shown in FIG. 10a obtained when a different disc was used in the apparatus.

FIGS. 10a and 10b show UCS chromaticity diagrams illustrating the gamut of colours realiseable in the colorimeter using different discs, as measured using a Minolta TV colour analyzer model TV2130. The circles show the loci of chromaticity coordinates obtained when the disc is rotated, and the spokes the loci obtained as the eccentricity of the disc with respect to the light source is varied. The centre of the gamut can be adjusted by varying the angular size of the coloured sectors, in FIG. 10a green is given the largest sector. As a result, the loci of coordinates obtained at high saturation shows a steep curve near green. The gamut was biased towards the areas of colour space where, in pilot work, colour preference was most frequently expressed. The gamut shown in FIG. 10b is the result of equal size sectors of colours in the disc and hence is more symmetrical. It could easily be altered to be more symmetric about a reference white, although the gamut would then be less extensive in the preferred range. Similarly it could be extended where necessary by the addition of further filters in the path of the light allowing the co-varying of luminance.

Provided the light source remains stable and the coloured filters are kept cool and do not deteriorate, the box can be calibrated and used to provide light of any chromaticity coordinates within the available gamut. It is necessary only to convert the u' and v' values to the appropriate disc angle and vertical position via a calibration graph similar to those shown in FIGS. 10a and 10b.

Figure 11A:
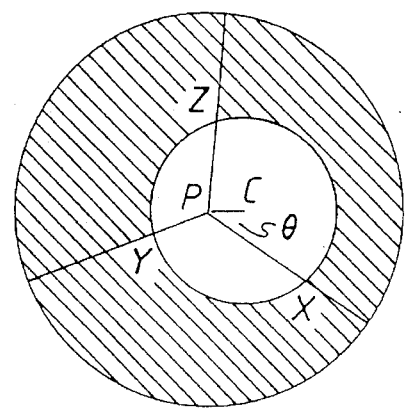
FIG. 11a shows a main face of a part of the apparatus shown in FIG. 3.
Figure 11B:
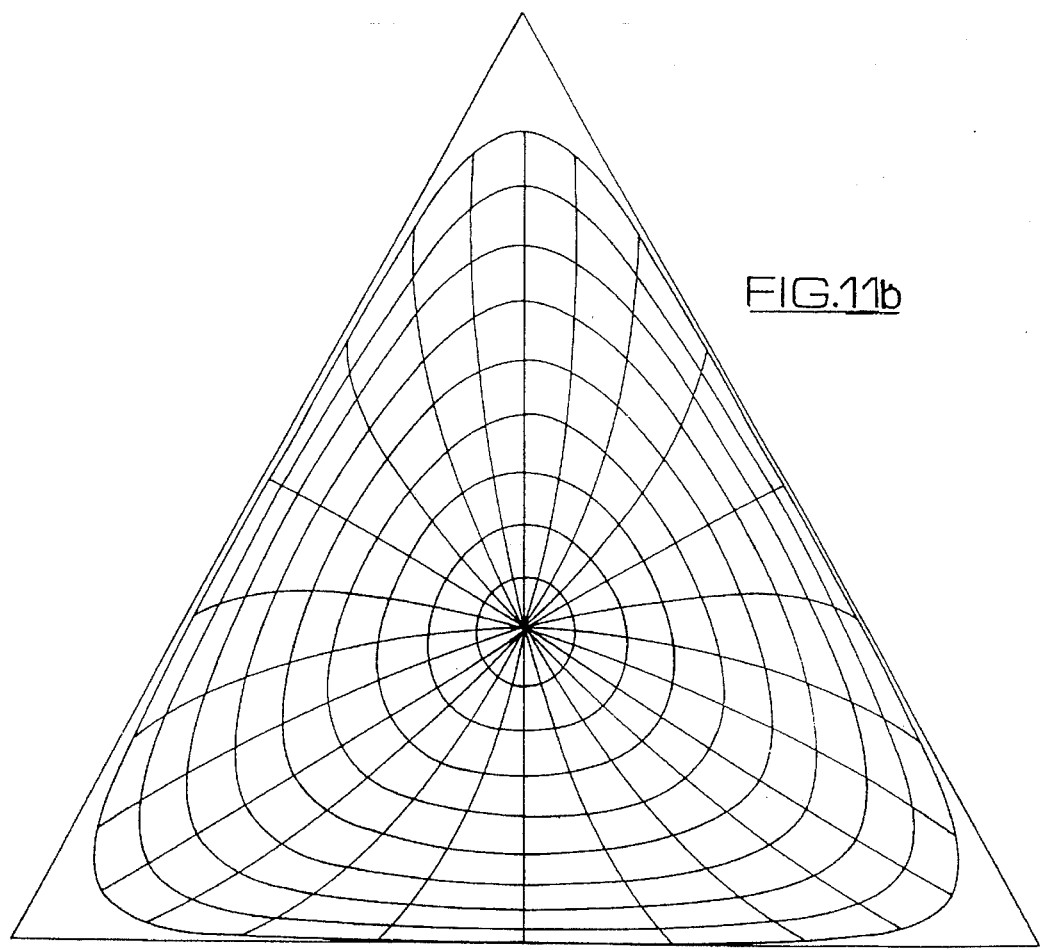

The geometry of the configuration is complex and hue and saturation are necessarily covaried to some extent. The extent of covariation increases with saturation. This is illustrated in FIG. 11a which shows an example of the simplest configuration. In this example a disc is divided into three radial sectors each 120° at the apex. The areas of the sectors which are illustrated, expressed as a function of x, the distance between the centre of the beam of light and the centre of the disc, will be given hereinafter. The graph in FIG. 11b shows a triangular surface which describes in baricentric coordinates the proportion of the areas of the smaller circle taken by the sectors PXY, PXZ and PYZ. The triangle can therefore be thought of as representing an arbitrary colour space, the coordinates of three primary colours at the apices. For example, the apices of the triangle might represent the coordinates of three filters in UCS coordinate space. At the centre of the space the three primary colours are mixed in equal proportion. The coordinate of the centre could be that of some reference white, in which case the distance from the centre would vary monotonically with the saturation of a particular hue. The concentric contours illustrate the way in which hue varies as the disc is rotated. If the coordinates of the three primaries are nearly equidistant from equal energy white in UCS coordinate space, the concentric contours can be made to resemble the loci of the coordinates of Munsell chips with similar chromaticity. In other words the hue can be varied, keeping saturation approximately constant. The spokes emanating from the centre illustrate the effect of varying the separation of the centre of the circular beam of light and the centre of the disc. When the separation is large the concentric loci do not approximate a circle and spokes do not approximate straight lines, reflecting the fact that the separation of hue and saturation can be achieved only approximately, and only over a limited gamut size. The largest locus shown is that obtained when PQ is equal to the radius of the beam of light, indicating that the full gamut represented by the triangle is not obtained until PQ exceeds the radius of the light beam.

Some colours can be strongly saturated, others cannot. There are saturated reds, for example, for which there is no yellow with equivalent saturation. There is therefore a limit to the size of gamut obtainable if hue and saturation are to be independently varied. It is sometimes necessary to trade-off the requirements for the separate manipulation of hue and saturation against the requirements for a large gamut size.

The disc shown in FIG. 11a illustrates one possible choice of trade-off, in which the sectors subtend equal angles at P of $2\pi/3$(120°). In FIG. 11a there is a circular light beam, with a centre C and a radius CX, and a disc, with a centre P and a radius greater than the diameter of the beam. If CX=1 and CP=x then the area of eccentric sector PXY is given by the following expression:

$$\tfrac{1}{2}(2\pi/3+\arcsin(x\sin\alpha)-\arcsin(x\sin\theta)+x\sin[\alpha-\arcsin(x\sin\alpha)]-x\sin[\theta+\arcsin(x\sin\theta)]$$

where $\alpha=2\pi/3+\theta$.
Similar expressions describe areas PXZ and PYZ.

FIG. 11b shows a baricentric plot illustrating the manner in which the proportion of the three eccentric sectors (PXY, PXZ, and PYZ) is affected by rotating the disc (varying $\theta$) and by translating the disc (varying the distance CP). The closed curves are contours of constant x with x=0 at the centre. The outermost curve shows the contour obtained when P lies on the circumference of the beam, i.e. when x=radius CX. The curves radiating from the centre are lines of constant $\theta$ at intervals of $\pi/12$(15°).

Figure 12A:
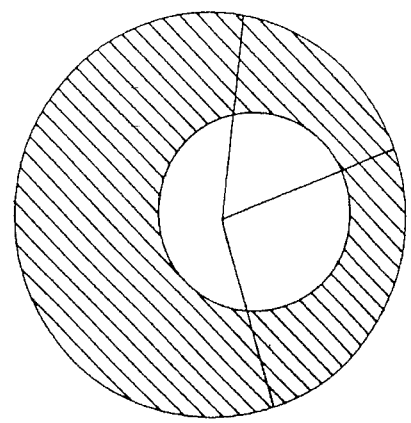
Figure 12B:
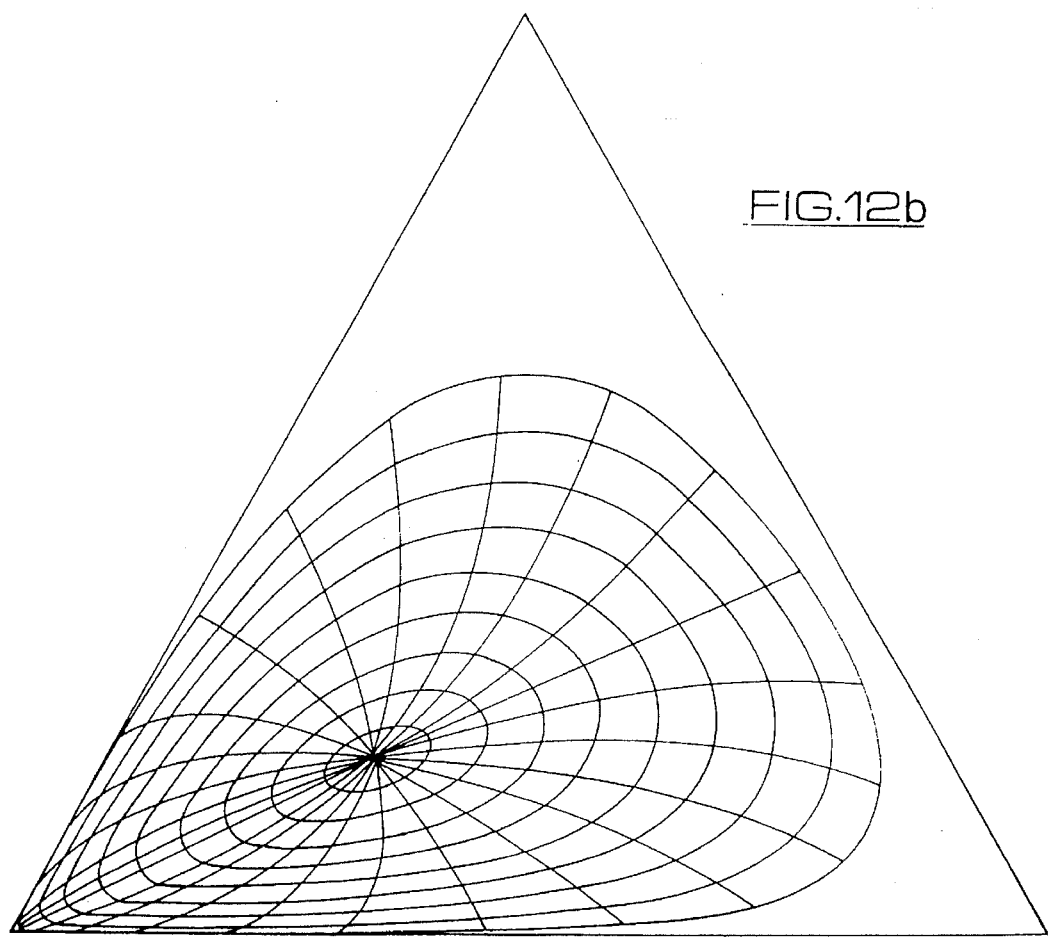

FIG. 12a and 12b illustrate the way in which the symmetrical arrangement in FIG. 11a and 11b is distorted by a choice of unequal sector angles. The graph shown in FIG. 12b is a baricentric plot showing the manner in which the proportion of the sectors is affected by rotating or translating the disc. The angles are those shown in FIG. 11a and used in the apparatus described in FIGS. 2 to 8.

Numerous modifications and variations will readily occur to the reader skilled in the art but which will not take the colorimeter outside the scope of the present invention. For example the number of primaries (and the number of sectors) may be increased to increase the independence of hue and saturation. Whether the addition complexity is justified depends on the gamut required and the use to which the colorimeter is put.

Figure 13A:
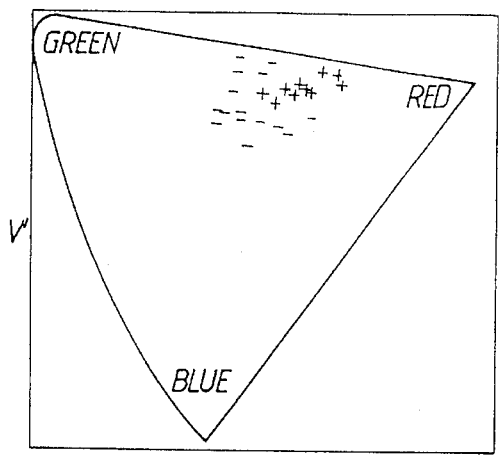
FIGS. 13a, 13b, 14a, 14b, 15a and 15b show experimental results of preferred tints selected by patients, in the form of UCS chromaticity diagrams.
Figure 13B:
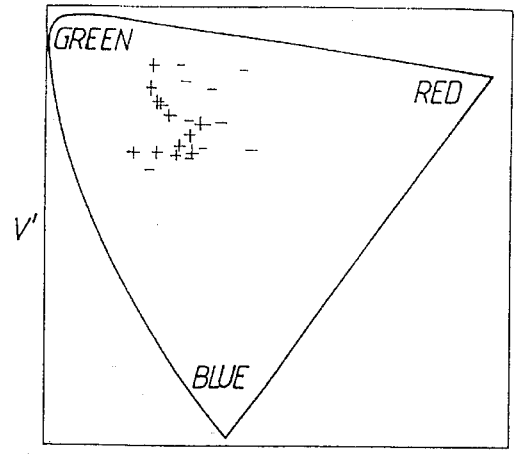

The colorimeter was used to examine a series of people referred by teachers, educational psychologists and optometrists to find the effects of colour on perceptual distortion. The subjects all found reading difficult, and complained of distortions of the page of text when reading. All had been examined by an optometrist and none needed correction for myopia, hyperopia, or astigmatism. FIG. 13a shows data from an eighteen year old girl. She was asked to rotate the wheel 34 of the colorimeter, varying hue, to see if she could find a setting in which the distortions on a page of text disappeared. The settings are shown with the symbol '+'. She was then asked to turn the wheel slowly until the distortions reappeared and the settings are shown with the symbol '−'. She did this repeatedly with hues of different saturation. There is a very small area of colour space in which her distortions disappeared. It is so small that it might be missed by a limited range of tinted glasses or overlays. FIG. 13b shows data from a fifteen year old boy. It was observed that the distortions disappear when the light is an unsaturated blue or a saturated green.

Figure 14A:
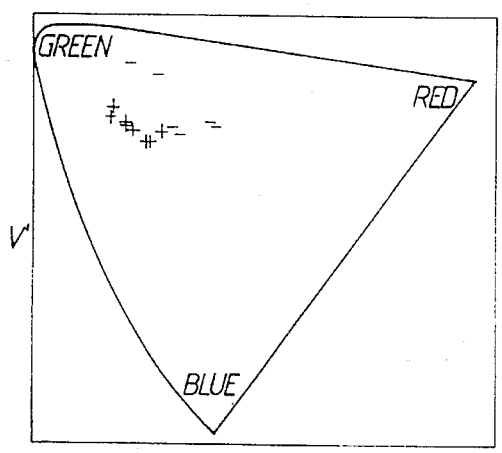
Figure 14B:
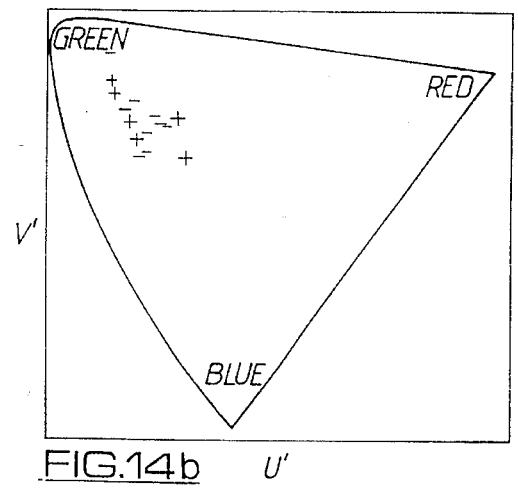
Figure 15A:
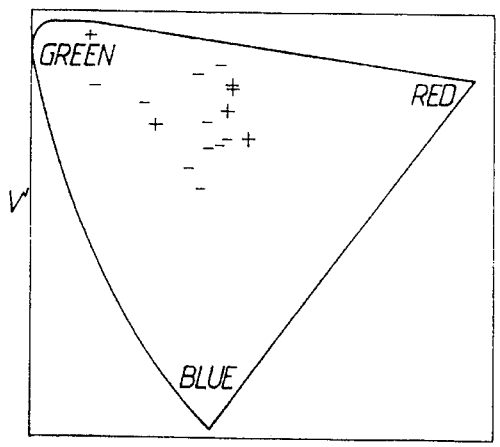
Figure 15B:
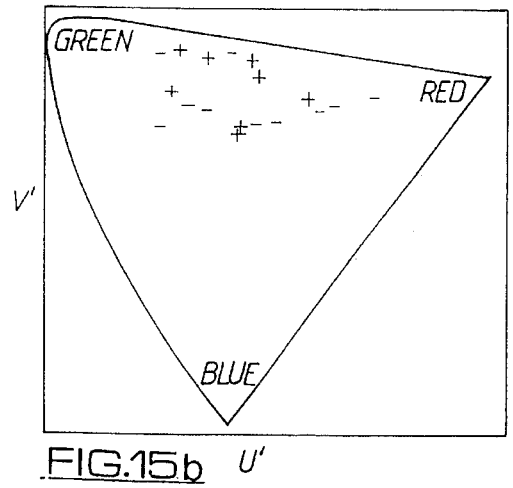

These data substantiate that the choices of colour are idiosyncratic and can be very specific. The colour choices can also be stable and reliable from one text to the next. FIGS. 14a and 14b show data from a ten year old girl obtained on two occasions one week apart.

The technique does not necessarily result in patches in colour space. It is quite possible for children to report distortions that are inconsistent and may relate to tiredness or other factors. FIGS. 6a and 6b present data for two boys, one aged nine and the other ten, showing an inconsistent scatter in colour space using the same technique as that used to obtain the settings shown in the previous Figures.

From the above observations it would seem that certain individuals are subject to distortions of text and that for some the distortion can disappear when the text has a particular colour. The colour is sometimes (but not always) specific, consistent, and yet different from one person to another.

It is quite difficult to obtain spectacles with the appropriate ophthalmic tint. It is necessary to take into account (1) the influence of coloured surfaces and (2) the colour of the illuminating source, be it fluorescent light or daylight or some combination of the two.

With a view to obtaining spectacles having an ophthalmic tint which matched the tint selected by means of the colorimeter, a set of filters may be used, prepared from seven coloured dyes selected so that lenses having photopic transmission of 50% when tinted have CIE 1976 hue angles that are approximately 50 degrees apart. The spacing is slightly closer in the area of the UCS chromaticity diagram most commonly selected by patients (turquoise) and slightly greater in the complementary area (red).

In addition to the seven coloured dyes, the set includes a dye with neutral density and one with ultraviolet absorption making a total of nine dyes.

Trial lenses each tinted with one of the seven coloured dyes or the neutral density dye have been prepared in sets with progressively increasing deposition of dye. At each level of deposition there are two lenses with identical spectral transmission. When these lenses are superimposed, the spectral transmission of the combination is similar to that of a single lens at the next level of dye deposition. The set of trial lenses therefore comprises a series of pairs in which the tint increases approximately logarithmically. The lenses with maximum deposition of dye, each have a photopic transmission of 50% under D65 standard daylight, except in the case of the yellow tint where the greatest deposition possible has a transmission of 74%. A single pair of lenses is tinted with the ultraviolet dye.

Thus combining several lenses tinted with the same dye, precision saturation can be achieved over a considerable range. An example of a series of combinations of trial lenses with progressively increasing tint is shown in Table 1.

TABLE 1

Combinations of trial tints yielding a series of increasing dye deposition shown in rows. (Lenses are numbered sequentially in order of increasing deposition.)

| | | | |
|---|---|---|---|
| 1 | | | |
| | 2 | | |
| 1 | 2 | | |
| | | 3 | |
| 1 | | 3 | |
| | 2 | 3 | |
| 1 | 2 | 3 | |
| 1 | | | 4 |
| | | | 4 |
| | 2 | | 4 |
| 1 | 2 | | 4 |
| | | 3 | 4 |
| 1 | | 3 | 4 |
| | 2 | 3 | 4 |
| 1 | 2 | 3 | 4 | etc. These combinations thus yield 31 levels of dye deposition with five filters.

Further by combining lenses tinted with different coloured dyes, tints with hue angles in between those of the seven dyes can be obtained. To approximate any given hue angle it is necessary to mix trial tints from only two dyes, those with hue angles nearest to the hue angle desired. This simplifies the selection of trial tints. It enables a hue mixed in the colorimeter to be matched very rapidly.

Where possible, the dyes selected are single chemical compounds, rather than mixtures. The dyes are therefore stable over time: they do not change colour in the tint bath as one chemical is exhausted before another.

Ophthalmic lenses are dyed to match the combination of trial lenses that best reduces syptoms. The same dyes are used for the ophthalmic lenses as those used for the trial lenses, so that the spectral transmission of each ophthalmic lens is identical to that of the combination of trial lenses.

Lenses tinted with the selected dyes and combinations of dyes have smooth spectral transmission functions, i.e. functions with few local maxima and minima. This reduces metamerism. The perception of colour is the result of brain mechanisms that compare the spectral reflectance of surfaces, discounting the contribution from the spectral power distribution of the illuminant so as to achieve a constant perception of colour under various illuminants. A tint with a smooth spectral transmission interferes minimally with the relative reflectance of surfaces. The disruption of colour perception should therefore be reduced.

Figure 16A:
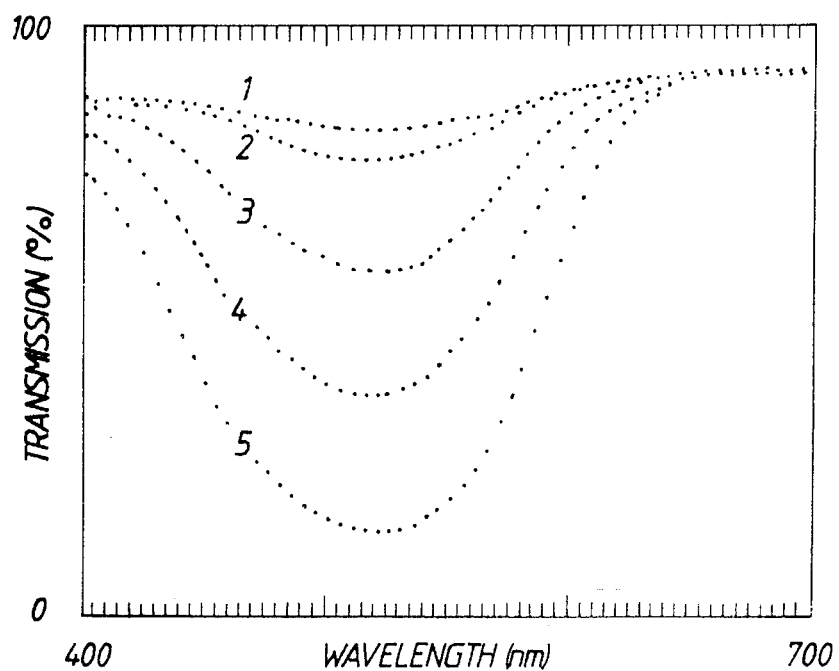
FIGS. 16a to 16g shows respective graphs of the transmission functions of a set of filters for use in conjunction with the apparatus shown in FIG. 3.
Figure 16B:
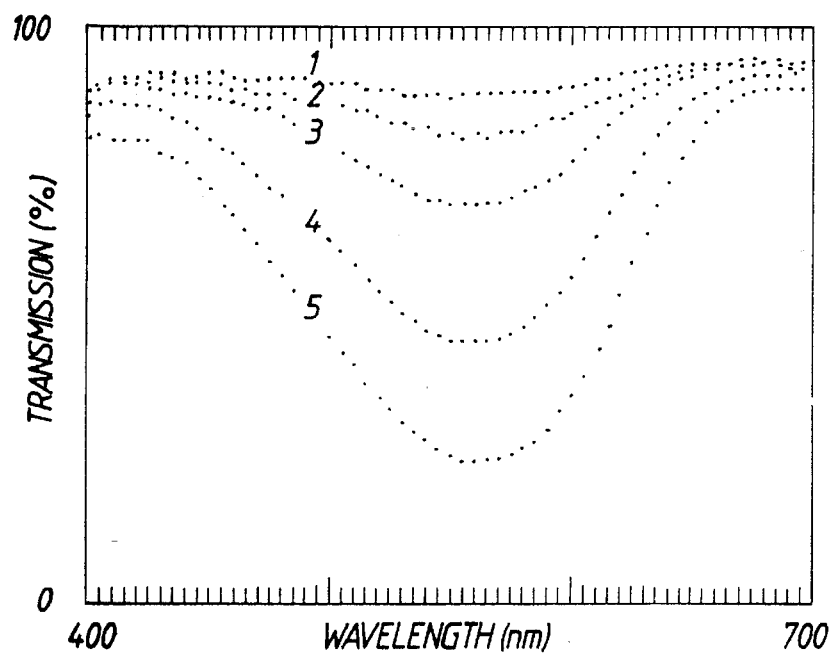
Figure 16C:
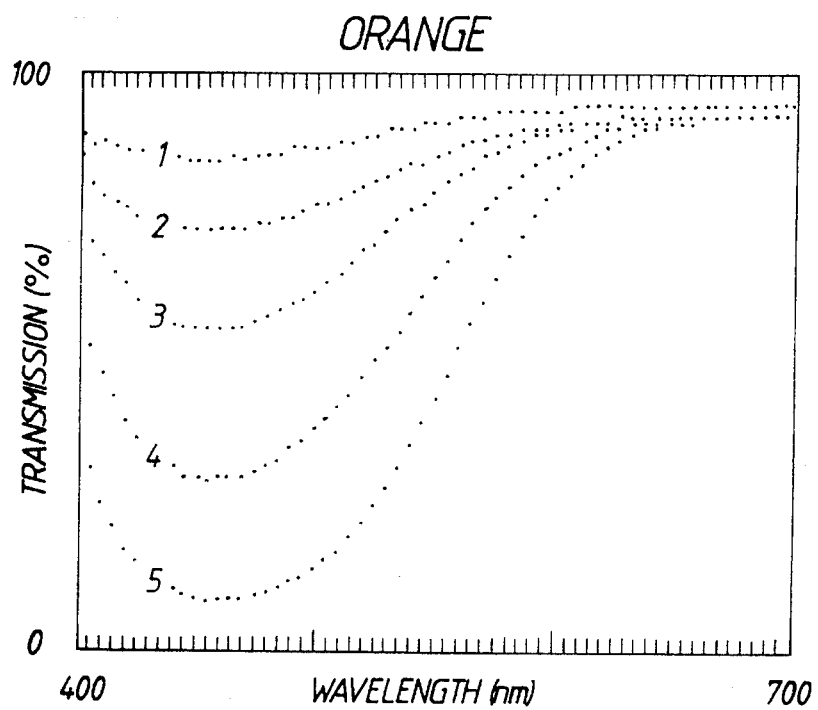
Figure 16D:
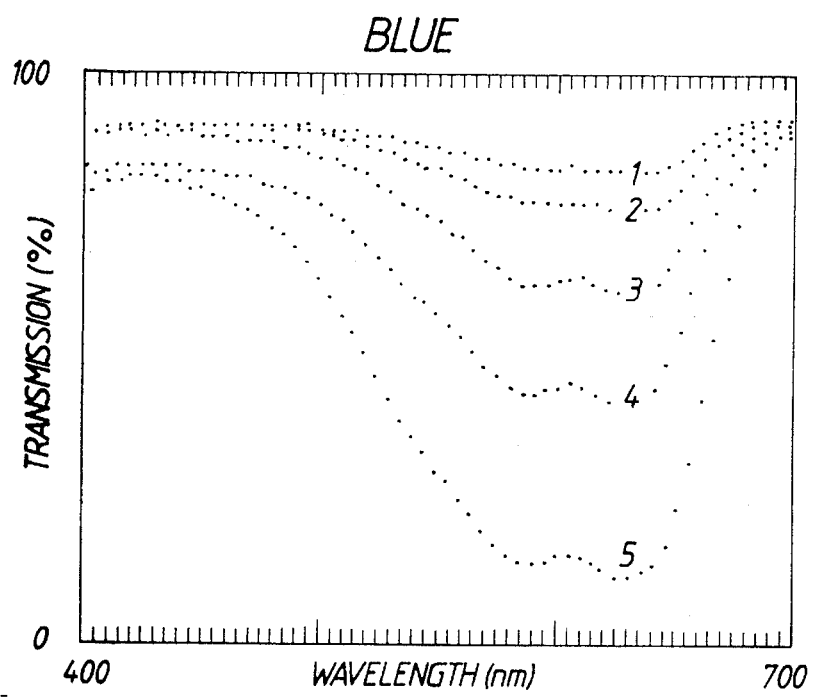
Figure 16E:
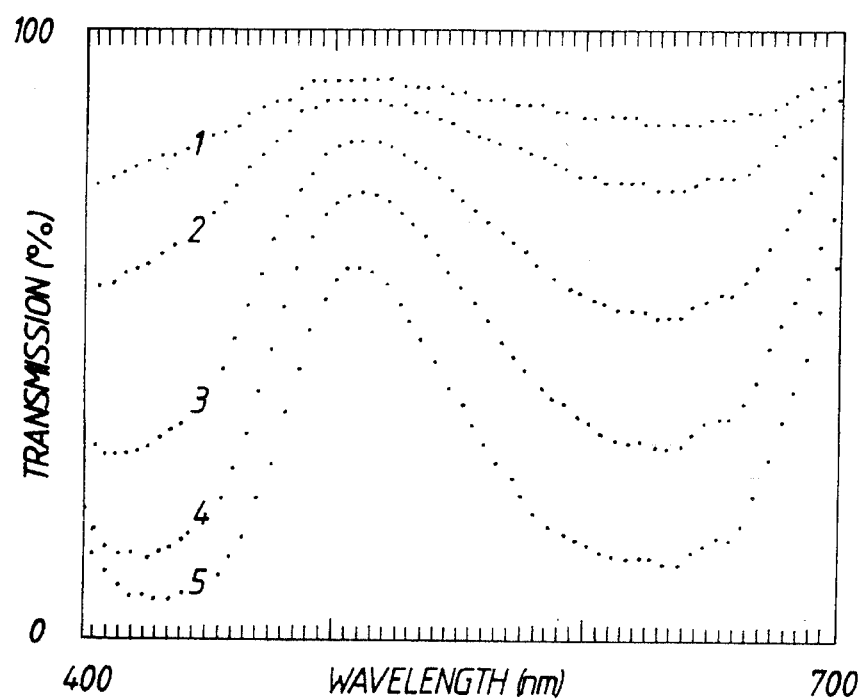
Figure 16F:
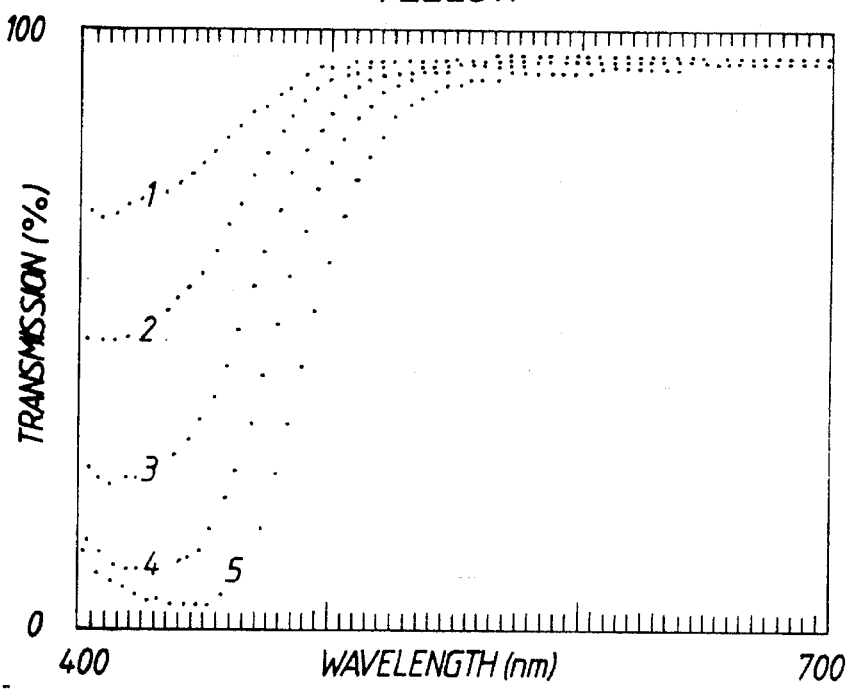
Figure 16G:
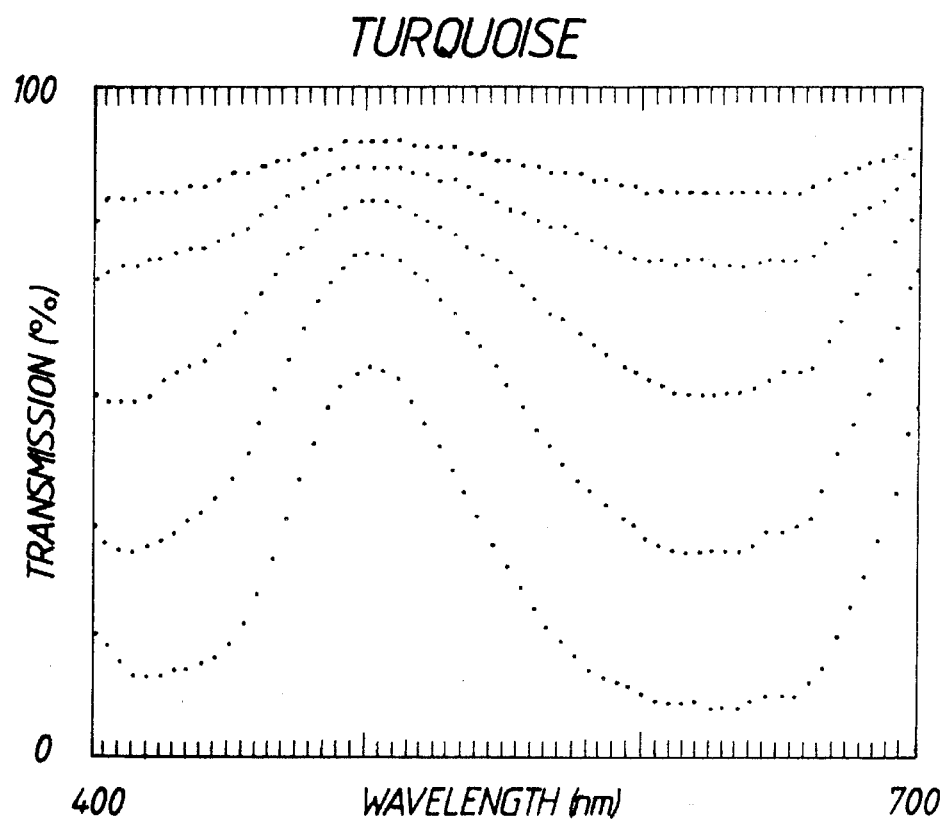

A preferred set of filters for use in matching an ophthalmic tint to be applied to lenses of spectacles in accordance with a tint selected by means of the colorimeter has the characteristics illustrated in FIGS. 16a to 16g. Thus the set comprises thirty-five filters in duplicate (for two eyes), there being seven colours each with five shades. For example, FIG. 16a, shows the spectral transmission functions of five filters each with the same hue of rose, but with different degrees of shading, each shade being substantially twice as intense as the next lesser degree of shading. Each plot shows transmission (as a percentage of full transmission) as a function of wavelength in nanometers. FIGS. 16b to 16g show the same functions for purple, orange, blue, green, yellow and turquoise. The UCS diagram of FIG. 17 shows the gamut of tints that can be obtained from different combinations of the filters, the area enclosed by line B shows the gamut realisable using six such filters. Overall transmission may be registered using neutral tints. The selected tint is thus maintained by a combination of filters from the set of filters to obtain the same tint, and the same dyes used for the filters may be applied to spectacle lenses to obtain the same resultant transmission function obtained from the said combination. Alternatively, it may be possible to obtain the desired transmission function, and the required mix of dyes, directly from the measurements of hue and saturation obtained from the colorimeter.

I claim:

1. Apparatus for obtaining a desired ophthalmic tint, comprising a light source, an enclosure, wherein said enclosure has internal surfaces that are white or a uniform color, a first aperture in the enclosure through which light from the light source may be directed into the enclosure, a second aperture in said enclosure through which the interior of the enclosure may be viewed, colored means positioned to affect light from the light source which passes through said first aperture, said colored means having regions that are colored differently to tint the light which passes through said first aperture to give it a hue and saturation which is dependent upon the areas of the colored means upon which light from the light source is incident, control means arranged to effect relative movement between the colored means and the light source to vary the hue and/or saturation of the tinted light, the colored means comprising a part which has the regions of different color such that when a main face of that part is viewed it appears to have regions which are colored differently, a first control of said control means, operation of which effects relative movement between the colored means and the light source to vary the hue of the tinted light while maintaining the saturation thereof substantially constant, and a second control of said control means, operation of which effects relative movement between the colored means and the light source to vary the saturation of the tinted light while maintaining the hue thereof substantially constant, the first and second apertures and the internal surfaces of the enclosure being so arranged that the tint of light observed through the second aperture is a mixture of the colors of light which enter through the first aperture, the mix being effected by multiple reflection of the light in the enclosure.

2. Apparatus according to claim 1, in which the colored means comprise a plurality of regions of respective different colours, each region being contiguous with two others along lines, and the plurality of lines of contiguity meeting at a common point.

3. Apparatus according to claim 2, in which the said regions are transmissive filters.

4. Apparatus according to claim 2 or claim 3, in which the said regions are parts of a circular disc.

5. Apparatus according to claim 4, in which the said regions are radial sectors of the disc.

6. Apparatus according to claim 5, in which the control means further comprise light directing means which serve to direct light towards an illuminated area that is moveable relative to the said regions so as to be incident upon parts of any two or more of the said regions.

7. Apparatus according to claim 6, in which the variation in hue is effected by a relative circular movement of the said area about the said common point, and the variation in saturation is effected by relative radial movement of the said area towards or away from the said common point.

8. Apparatus according to claim 1, further comprising a set of coloured filters, in which at least a first one of the set has a colouring strength which is greater than that of a second one of the set, and a third one of the set has a colouring strength which is greater than the said first one of the set, so that a linear or logarithmic increase in colouring strength is obtained from successive selections from the set as follows: firstly the said second filter; secondly the first and second filters together; thirdly the said third filter on its own; then the third and first filters; then the third and second filters, then the first, second and third filters.

* * * * *

UNITED STATES PATENT AND TRADEMARK OFFICE
CERTIFICATE OF CORRECTION

PATENT NO. : 5,528,431
DATED : June 18, 1996
INVENTOR(S) : WILKINS

It is certified that error appears in the above-indentified patent and that said Letters Patent is hereby corrected as shown below:

On the cover page, the Assignee Section which reads:
"Cerium Group Limited of Hill House, London, United Kingdom"
Should be corrected to read:
--Cerium Visual Technologies Limited, Kent, England and
The Medical Research Council, London, England--

Signed and Sealed this

Nineteenth Day of August, 1997

Attest:

BRUCE LEHMAN

Attesting Officer

Commissioner of Patents and Trademarks